(12) United States Patent
Smith et al.

(10) Patent No.: US 8,301,019 B2
(45) Date of Patent: Oct. 30, 2012

(54) FRAGRANCE EMANATION SYSTEM

(75) Inventors: Stephen Smith, Dublin, OH (US);
David Baraky, New Albany, OH (US);
Robert Bussom, Pickerington, OH (US);
Todd Wambach, Inner Grove Heights, MN (US); Harry Slatkin, New York, NY (US)

(73) Assignee: Bath & Body Works Brand Management, Inc., Reynoldsburg, OH (US)

( * ) Notice: Subject to any disclaimer, the term of this patent is extended or adjusted under 35 U.S.C. 154(b) by 990 days.

(21) Appl. No.: 11/906,418

(22) Filed: Oct. 2, 2007

(65) Prior Publication Data
US 2008/0253755 A1 Oct. 16, 2008

Related U.S. Application Data

(63) Continuation-in-part of application No. 10/656,752, filed on Sep. 4, 2003, now Pat. No. 7,277,626.

(51) Int. Cl.
*A01G 13/06* (2006.01)
*A61M 16/00* (2006.01)
*A24F 25/00* (2006.01)

(52) U.S. Cl. .......................... 392/386; 392/390; 239/44

(58) Field of Classification Search .................. 392/386, 392/387–406, 324–337; 239/13–44; 43/131; 424/76.3; 422/125, 439, 446; 187/396; 219/401
See application file for complete search history.

(56) References Cited

U.S. PATENT DOCUMENTS

| | | |
|---|---|---|
| 2,176,345 A | 10/1939 | Hurwitt |
| 4,663,315 A | 5/1987 | Hasegawa et al. |
| 4,968,487 A | 11/1990 | Yamamoto et al. |
| D314,045 S | 1/1991 | DeLuca et al. |
| 5,038,394 A | 8/1991 | Hasegawa et al. |
| D330,075 S | 10/1992 | Kuhn |
| 5,222,186 A | 6/1993 | Schimanski et al. |
| D357,330 S | 4/1995 | Wong et al. |
| D361,126 S | 8/1995 | Fukada |
| D371,517 S | 7/1996 | Narayanan |
| 5,595,503 A | 1/1997 | Pittman et al. |

(Continued)

FOREIGN PATENT DOCUMENTS

EP 0420144 A1 4/1991

(Continued)

OTHER PUBLICATIONS

European Search Report for application No. EP 08754736 dated May 27, 2011.

*Primary Examiner* — Daniel L Robinson
(74) *Attorney, Agent, or Firm* — Ward & Zinna, LLC

(57) ABSTRACT

The fragrance emanation system includes a container for holding preferably a fragranced liquid or gel, a housing for holding the container, and a wick. The housing contains a socket for attaching to the container, a cavity for receiving the container and a door for enclosing the container. One end of the wick protrudes from the container. An electrical circuit is included having a heater for heating the protruding end of the wick and electrical connectors coupled to the circuit to receive current from a power source to provide the current to the heater. The heater heats and evaporates the liquid within the wick, thereby accelerating the emission of vapors from the evaporated liquid. The door includes a window, a bottom and a mechanism for holding the door closed to assist in holding the container in engagement with the socket.

11 Claims, 5 Drawing Sheets

U.S. PATENT DOCUMENTS

| | | |
|---|---|---|
| 5,647,053 A | 7/1997 | Schroeder et al. |
| 5,710,406 A * | 1/1998 | Garris et al. .................. 219/267 |
| 5,926,614 A | 7/1999 | Steinel |
| 5,955,710 A | 9/1999 | DiFranza |
| 6,236,807 B1 | 5/2001 | Ruffolo et al. |
| D452,732 S | 1/2002 | Basaganas |
| D454,628 S | 3/2002 | Basaganas |
| D492,021 S | 6/2004 | Basaganas |
| 7,171,923 B2 * | 2/2007 | Hayakawa et al. ......... 122/20 R |
| 7,277,626 B2 * | 10/2007 | Pesu et al. ..................... 392/390 |
| 7,544,331 B1 * | 6/2009 | Pettaway ....................... 422/125 |
| 2008/0253755 A1 * | 10/2008 | Smith et al. .................. 392/386 |

FOREIGN PATENT DOCUMENTS

| | | |
|---|---|---|
| EP | 1547464 A1 | 6/2005 |
| WO | WO 2005107824 A2 | 11/2005 |
| WO | WO 2006105383 A2 | 10/2006 |
| WO | WO 2006105396 A1 | 10/2006 |

* cited by examiner

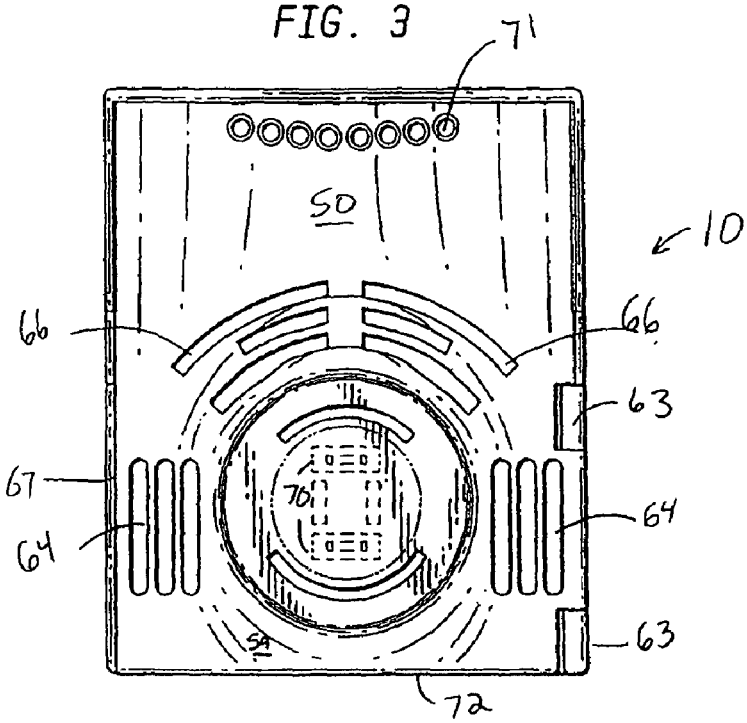
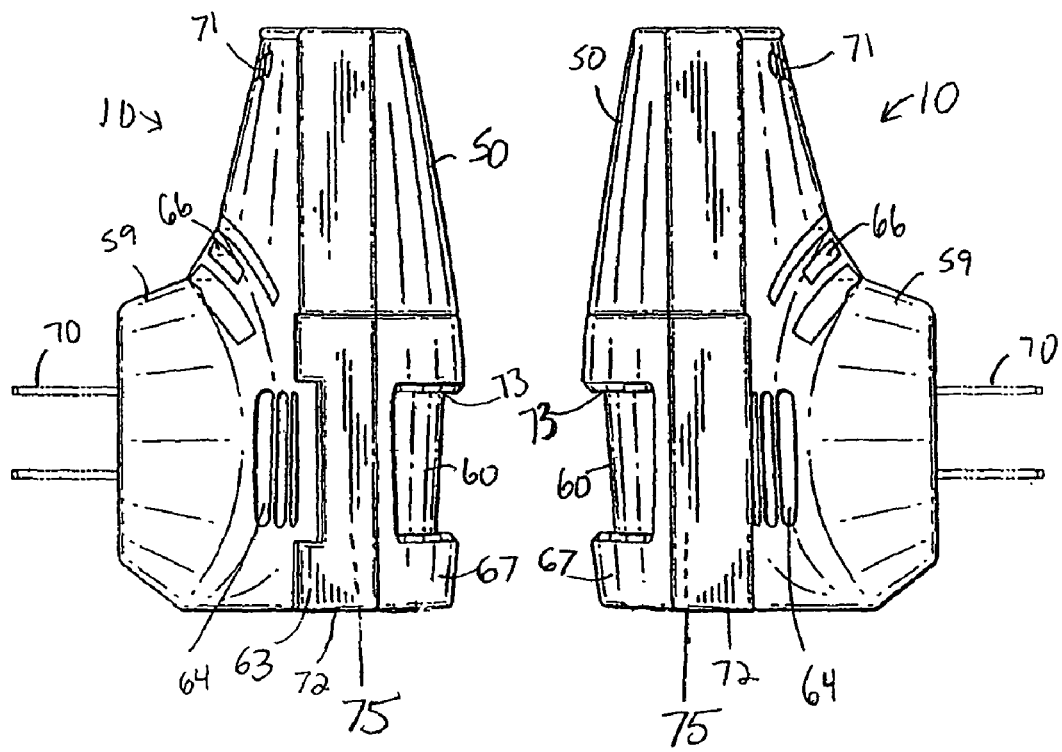

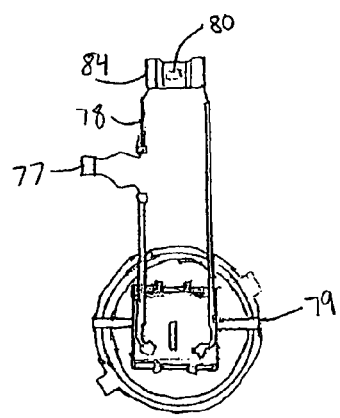
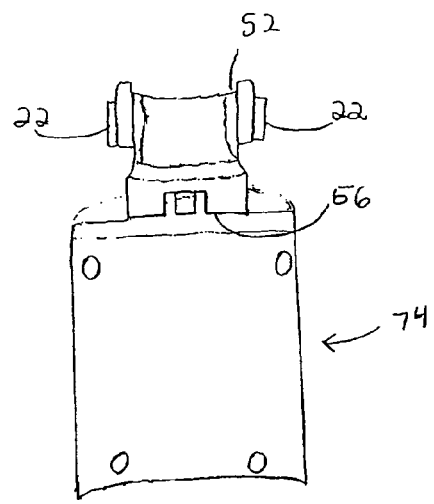
FIG. 6          FIG. 7
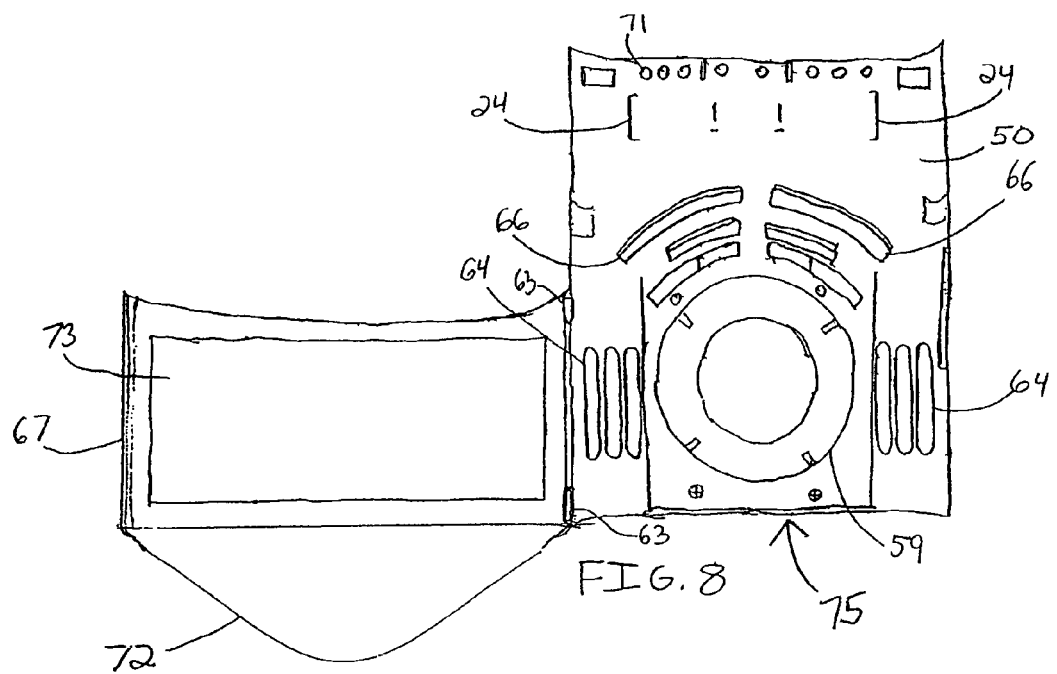
FIG. 8

FRAGRANCE EMANATION SYSTEM

CROSS-REFERENCE TO RELATED APPLICATIONS

This application is a continuation-in-part of application Ser. No. 10/656,752, filed Sep. 4, 2003, now U.S. Pat. No. 7,277,626 which is incorporated herewith.

TECHNICAL FIELD OF THE INVENTION

The present invention relates in general to electric air freshener systems and in particular to a new and useful fragrance emanation system using a wick evaporation system.

BACKGROUND OF THE INVENTION

Air fresheners have existed for quite some time. Generally, an air freshener is used to emit a pleasant aroma into a room or enclosed area. The aroma may create a mood, invoke a psychological response and/or mask unpleasant odors. In some instances, aromas are used for therapeutic purposes.

Wick-based air freshener systems are known in the art for dispersing the vapors of liquids into the air. Such systems are often used in and around the home in conjunction with a wide array of liquids, ranging from insect repellant to fragrance oils. Typically, in such systems, one end of a wick is partially submerged in the liquid to be dispersed. The liquid is contained in any suitable container. The partially submerged portion of the wick absorbs the liquid, some of which is drawn up by capillary or wicking action through the exposed, non-submerged portion of the wick. The exposed portion of the wick is locally heated, often by means of a ring-shaped heater that fits over the wick. This causes the liquid that has diffused into the exposed portion of the wick closest to the heating element to evaporate into the surrounding air. Continual application of heat to the exposed portion of the wick results in an evaporation/absorption process that continues until the liquid is fully consumed.

The aforementioned method of using a heating element to motivate the evaporation of an aromatic or fragrant compound into the atmosphere is one of the most common methods for implementing an air freshener. For example, one known device utilizes scented liquid held in a bottle. The bottle contains a wick that is submerged in the scented liquid at one end while protruding through the top of the bottle at the other end. The wick draws up the scented liquid by means of capillary action. The end of the wick that protrudes through the top of the bottle is located next to a heating element so that the drawn up scented liquid is evaporated by the heat emitted from the heating element. This type of air freshener is usually plugged into a standard wall outlet, which provides both power and physical support. The wall outlet supplies power to the heating element in the form of alternating current ("AC"), which as previously mentioned, heats the fragrant compound. The heat causes the fragrant compound to evaporate and disperse into the atmosphere, thereby emitting an aroma.

Known air freshener systems generally contain a fragrance bottle that is exposed to the user at all times. The bottle is attached to the air freshener with the wick extending from the bottle into the air freshener. Having the fragrance bottle exposed to the user allows breakable fragrance bottles to fall and shatter on the floor. This also allows easy access for children to be exposed to the fragrance bottle and its contents. In addition, liquid fragrance may drip on the floor and create a harmful, dangerous and/or unsanitary environment.

Air fresheners may utilize a variety of heating elements. For example, some air fresheners utilize positive temperature coefficient ("PTC") heating elements. Alternatively, a series of resistors may be used to heat the fragrant compound. It is also known to use resistors to heat a ceramic block, which in turn heats a wick saturated with a scented liquid. Using a power source (such as a standard wall outlet) in conjunction with one or more resistors has also proven effective.

As discussed above, known air freshener systems contain exposed, drip prone, often glass or otherwise breakable fragrance containers that hang from the system. As such, there is a clear need for a device that securely encloses the fragrance container within the device.

There is also a clear need for a device that allows the user to determine the amount of liquid fragrance left in an enclosed fragrance container, such that the desirability of enclosing the fragrance container within the device does not require forgoing the ability to view the fragrance container. Additionally, there is a need for a device that contains a door, which snaps closed and securely encapsulates the fragrance container and contains an aperture or transparent or translucent window to allow for a clear view of the fragrance container without the need to open the door.

SUMMARY OF THE INVENTION

The present invention preferably includes a container for holding a fragrant liquid, a housing for holding the fragrance container, and a wick with one of its ends protruding from the fragrance container. The housing preferably contains a socket for attaching the fragrance container, a cavity for receiving the container and a door for enclosing the container. An electrical circuit is also preferably included having a heater for heating the protruding end of the wick. Additionally, the electrical circuit preferably contains electrical connectors coupled to the circuit in order to receive current from a power source, which also provides the current to the heater. The heater heats the wick, thereby heating the liquid, which has traveled up through the wick via capillary action from the fragrance container, thus accelerating the emission of vapors from the evaporated liquid.

The door optimally includes a window, a mechanism for holding the door closed and a bottom, which assists in holding the fragrance container in engagement with the socket.

One embodiment of the heater includes at least one resistor and is made of a ceramic material. At least one vent and one air intake are included in the housing to facilitate release of the aroma.

The fragrance container includes a threaded neck. The socket of the housing is also threaded, such that the fragrance container can be screwed into the housing after it is placed through the open door and into the cavity of the housing. Alternatively, the socket of the housing may contain an annular lip for holding the fragrance container in engagement with the socket.

Thus, it is an object of the present invention to provide a liquid fragrance emanation system.

It is also an object of the present invention to heat a wick that is submerged in a scented liquid in order to evaporate the scented liquid, thus providing an aroma.

It is also an object of the present invention to protect the fragrance container from accidentally falling and breaking.

It is also an object of the present invention to prevent any liquid fragrance from escaping either the fragrance container or the plastic housing.

It is also an object of the present invention to encapsulate the fragrance container within the fragrance emanation system by providing an enclosing mechanism.

It is also an object of the present invention to allow the user to determine the amount of liquid fragrance left in the fragrance container, while the fragrance container remains enclosed within the housing of the device.

In addition, it is an object of the present invention to provide a fragrance emanation system having an aesthetically pleasing design.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

SUMMARY OF THE DRAWINGS

A further understanding of the present invention can be obtained by reference to a preferred embodiment, along with some alternative embodiments, set forth in the illustrations of the accompanying drawings. Although the illustrated embodiments are merely exemplary of systems for carrying out the present invention, the organization and method of operation of the invention in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings.

FIG. 3 is a back view of the fragrance emanation system in accordance with one embodiment of the present invention;

FIG. 4 is a left side view of the fragrance emanation system in accordance with one embodiment of the present invention;

FIG. 5 is a right side view of the fragrance emanation system in accordance with one embodiment of the present invention;

FIG. 6 is a front view of a circuit insert in accordance with one embodiment of the present invention;

FIG. 7 is a front view of a heater assembly insert in accordance with one embodiment of the present invention;

FIG. 8 is a front view of the fragrance emanation system with the door in an open position and with all inserts removed in accordance with one embodiment of the present invention;

DETAILED DESCRIPTION OF THE PREFERRED EMBODIMENTS

Figure 1:
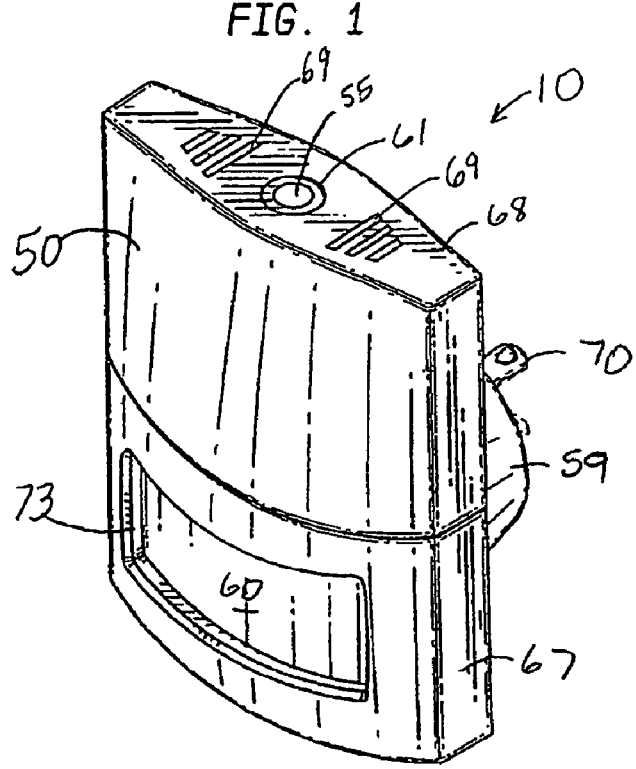
FIG. 1 is a perspective view of the fragrance emanation system in accordance with one embodiment of the present invention.

A detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific functional details disclosed herein are merely representative, yet in that regard, they are deemed to afford the best embodiment for purposes of disclosure and to provide a basis for the claims herein which define the scope of the present invention.

Moreover, well known methods and procedures for both carrying out the objectives of the present invention and illustrating the preferred embodiment are incorporated herein but have not been described in detail as not to unnecessarily obscure novel aspects of the present invention.

Referring to FIGS. 1-5, the fragrance emanation system of the present invention is generally designated 10, and comprises a multi-part plastic hollow housing 50. However, housing 50 may be made of any appropriate material. A generally circular plug portion 59 of housing 50 contains plug blades 70 in order to transfer electricity from the wall outlet to fragrance emanation system 10. Vertical air intakes 64 and substantially horizontal air intakes 66 are disposed in plastic housing 50 and are surrounding cylindrical plug portion 59. Additionally, circular air intakes 71 are provided at the top of the backside of the invention as shown in FIG. 3. The air intakes are provided to create airflow throughout fragrance emanation system 10 and may be any appropriate shape, number or size and in any appropriate location.

Figure 2:
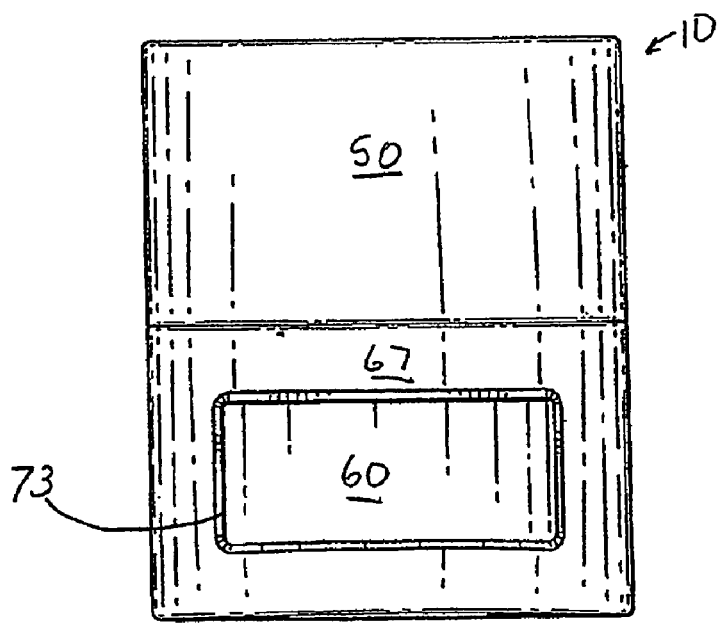
FIG. 2 is a front view of the fragrance emanation system in accordance with one embodiment of the present invention.

An enclosing mechanism or door 67 is preferably attached to plastic housing 50 via a hinge 63. Hinge 63 is located on the left side of fragrance emanation system 10, although hinge 63 may be located on the right side, or even on the top or the bottom of door 67. Thus, when looking at fragrance emanation system 10 from the front, as shown in FIG. 2, door 67 preferably opens from right to left. Door 67 is useful to assist in holding fragrance container 60 in place and may be opened when fragrance container 60 needs to be replaced. Furthermore, a plastic flange 72 is preferably attached to the bottom of door 67. Although plastic is described herein, flange 72 may be made from any appropriate material. When door 67 is in the closed position, flange 72 not only serves as a platform that provides added support to the bottom of fragrance container 60, but also in conjunction with housing 50 forms a cavity 75 inside housing 50, which is able to receive fragrance container 60. Door 67 and flange 72 prevent fragrance container 60 from accidentally falling and shattering as well as store or return any liquid that has escaped fragrance container 60 within housing 50. Additionally, door 67 optionally includes an aperture or window 73, which may be open or covered with a transparent or translucent material. Window 73 on door 67 provides a user with a simple way to assess the amount of gel or liquid 65 left in fragrance container 60, while fully containing fragrance container 60 within housing 50. Additionally, door 67 has a mechanism (not shown) to hold door 67 in a closed position when desired.

Housing 50 preferably includes a flat cover 68 containing vapor vents 69 to allow for the dissipation of fragrance vapors. Cover 68 contains sides that are preferably rectangular that widen into a circular shape towards the middle in order to conform to the shape of fragrance container 60. This shape helps create a unique and decorative fragrance emanation system 10 as it rests near a wall, supported by a wall socket.

Cover 68 preferably includes a plurality of air vents 69. In addition, in the middle of cover 68, there exists a circular opening 61 larger than the upper end 55 of the wick, which also serves as an air vent. The air vents are provided to release the vaporized fragrance from fragrance emanation system 10 and may be any appropriate shape, number or size and in any appropriate location.

As shown in FIGS. 6-8, housing 50 preferably contains a heater assembly 52 that is in close proximity to the upper end 55 of the wick. Heater assembly 52 is preferably semi-circular in design. However, heater assembly 52 may be any appropriate shape. Upper end 55 of the wick engages passage or opening 57 near heater assembly 52.

In addition, as illustrated in FIG. 7, heater assembly insert 74 preferably includes a socket 56, which can either utilize a snap fit or reverse thread design. The socket 56 receives the fragrance container 60 (not shown) as described in reference to FIG. 10. Moreover, heater assembly insert 74 contains preferably two annular grooves 22, which are used to securely attach heater assembly insert 74 to housing 50. Additionally, heater assembly insert 74 may be made from any appropriate material. Furthermore, a blade assembly 79 is preferably connected via a wire 78 to heater 80 and is used to support blades 70 (not shown).

In FIG. 8, door 67 is shown in operation and flange 72 is illustrated as providing the bottom to housing 50. In addition, preferably two annular rims 24 extend outwardly from inside housing 50.

In combination, the elements in FIGS. 6-8 illustrate the interior of hollow plastic housing 50. The ceramic body 84 fits in heater assembly 52 of heater assembly insert 74. Annular groove 22 then receives and snap fits into annular rim 24. This allows opening 57 to be snap fit inside housing 50, which then allows for ceramic body 84 to be securely attached to opening 57 within housing 50. At the same time, blade assembly 79 slides into and attaches to plug portion 59, where blades 70 (not shown) protrude outwardly from plug portion 59.

Figure 9:
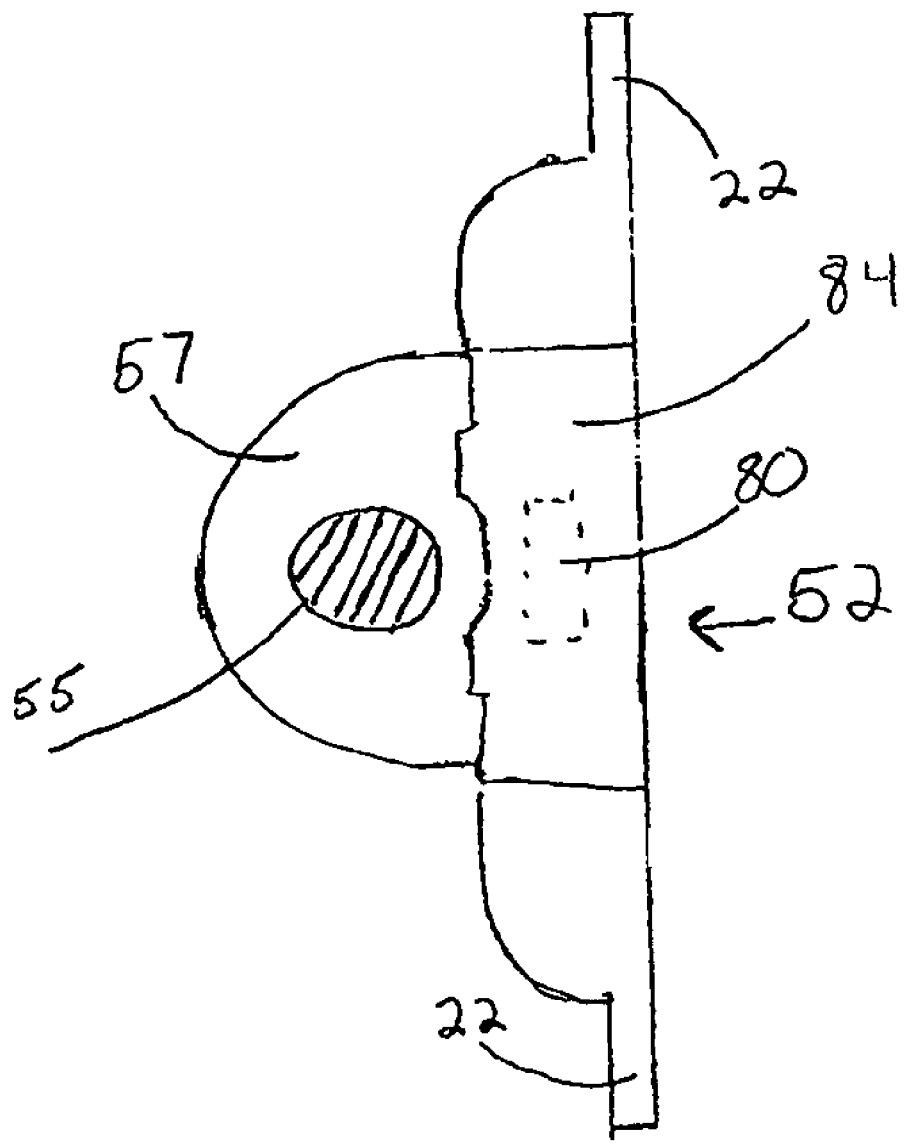
FIG. 9 is a top view of the heater assembly in accordance with one embodiment of the present invention.

As illustrated in FIG. 9, a preferred embodiment of heater assembly 52 comprises a heater 80, which is surrounded by a ceramic potting material body 84. However, various other appropriate heating assemblies may be used for the present invention. Additionally, body 84 also may be snapped into place by a preferably plastic heater assembly insert 74 and become attached to heater assembly 52 so it is adjacent to opening 57 for receiving the upper end 55 of the wick. Opening 57 may be slightly larger than the outer diameter of the upper end 55 of the wick to allow easy insertion of a new wick when liquid 65 in fragrance container 60 has been depleted.

Figure 10:
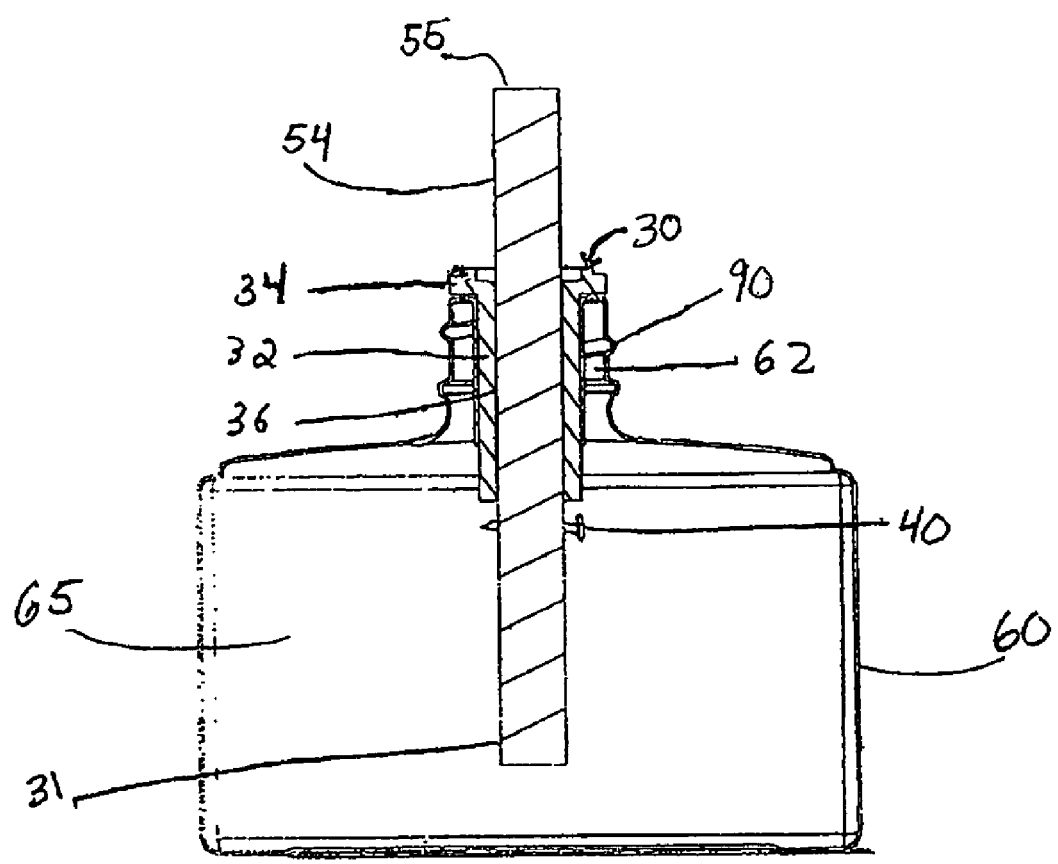
FIG. 10 is a partial sectional view of the fragrance container in accordance with one embodiment of the present invention.

As shown in FIG. 10, fragrance container 60 is advantageously made of glass. However, any material or container that is appropriate to contain a liquid, in particular, air freshening liquid, to be evaporated from the unit, may be used. The wick arrangement of the present invention includes a retaining ring 30 having a lower cylindrical portion 32, which closely engages by press fit and/or by use of adhesive into neck 62 of container 60 to prevent the removal of wick 54.

Ring 30 is preferably made of polypropylene or other high strength synthetic material such as nylon, and has an upper flange 34 forming the top of neck 62 of fragrance container 60. Ring 30 has an opening 36 extending through its axis that preferably has a diameter slightly less than the outer diameter of the flexible fibrous wick 54. This allows the lower portion of wick 54 to be firmly held in opening 36. Thereby upper end 55 of wick 54 extends through and protrudes from neck 62 in order to be heated. Additionally, wick 54 may be composed of cotton, cellulose, polyester or any known wick material.

Optionally, a steel pin 40 may be inserted through the fibrous wick 54 just below retaining ring 30 to securely hold wick 54 in place. Plastic or other sufficiently strong material may also be used for pin 40. Pin 40 is preferably long enough to extend radially through wick 54 by an amount sufficient to preclude extraction of wick 54, upwardly through retaining ring 30. This, in conjunction with the secure fixing of ring 30 to neck 62, prevents the extraction of the wick from fragrance container 60 and prevents refilling of fragrance container 60 with appropriate or inappropriate liquids. Pin 40 extends through skirt or sleeve 31, which encompasses wick 54 for added strength and resistance to removal of wick 54.

Further, the polypropylene retaining ring 30 may have a cylindrical portion 32 that is slightly greater in diameter than the inner passage through neck 62 so that a firm force is required to push ring 30 into neck 62. This simultaneously contracts the cylindrical portion 32 of neck 62 and, with wick 54 in place, effectively squeezes wick 54 even more firmly within opening 36. At the same time, the force fit is achieved, preferably without adhesive.

Reverse screw thread 90 is preferably included on neck 62 of fragrance container 60. When viewing fragrance container 60, which contains reverse screw thread 90 on neck 62, from above, the fragrance container 60 must be turned clock-wise to tighten it onto the housing and counter-clockwise to loosen and remove it. Optionally, neck 62 of fragrance container 60 and socket 56 may contain forward screw threads. Therefore, both forward and reverse screw thread containers may be used in fragrance emanation system 10.

During operation, fragrance emanation system 10 is energized by receiving electricity through electrical plug blades 70. Blades 70 are configured to be plugged into an electric wall outlet. Blades 70 both supply electricity to, and support fragrance emanation system 10 on the wall. Additionally, blades 70 are made to rotate at least 90 degrees in order to adapt to both a horizontal and a vertical electric wall outlet. When blades 70 are in either position, fragrance container 60 may always be located on the bottom of fragrance emanation system 10 and air vents 69 may always remain on the top.

Electrical power is drawn through blades 70 to heater 80. Blades 70 are preferably connected to heater 80 by means of electrical conducting wire 78 and resistor 77 all of which are connected in series as illustrated in FIG. 6. Heater 80 heats upper end 55 of wick 54 and fragrance emanation system 10 begins to dispense vaporized fragrance. Liquid 65 continues to evaporate near upper end 55 of wick 54 because of the heat that is provided by heater 80. Liquid 65 is replenished by capillary action as more liquid 65 is absorbed up from fragrance container 60 toward the upper end 55 of wick 54.

While the present invention has been described with reference to the preferred embodiment and alternative embodiments, which have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

We claim:

1. A liquid emanation system comprising:
    a container for holding a liquid;
    a housing, said housing having a socket for attaching to a neck of said container thereby supporting said container within said housing, said housing further comprising a top wall and side walls defining a cavity for receiving said container;
    a door hingedly coupled to said housing for enclosing said container within said cavity when the door is in a closed position and for accessing said cavity when the door is in an opened position, wherein said door comprises a vertical wall and a horizontal flange extending orthogonally from a bottom edge of said vertical wall, wherein said flange supports a base of said container, and wherein said vertical wall comprises a window aligned with said container for enabling said container to be viewed through said window;

a wick having a lower end extending into said container and an upper end protruding from said container, wherein said wick draws said liquid to said upper end of said wick; and an electrical circuit having a heater for heating said protruding end of said wick;

wherein said heater heats said upper end of said wick and thereby heats said liquid, accelerating the emission of vapors of said liquid.

2. The system in accordance with claim 1 wherein said door further comprises a mechanism for retaining said door in the closed position to assist in holding said container in engagement with said socket.

3. The system in accordance with claim 1 wherein said liquid is scented oil and said vapors emit an aroma.

4. The system in accordance with claim 1 wherein said heater comprises a ceramic material.

5. The system in accordance with claim 1 wherein said housing further includes at least one vent to facilitate release of said vapors.

6. The system in accordance with claim 1 wherein said housing further includes at least one air intake to facilitate release of said vapors.

7. The system in accordance with claim 1 wherein said container further comprises a threaded neck and said socket of said housing is threaded so that said container can be screwed into said housing.

8. The system in accordance with claim 7 wherein said threaded neck of said container is a reverse thread and said thread of said housing is a reverse thread so that said container can be screwed into said housing.

9. The system in accordance with claim 1 wherein said socket of said housing contains an annular lip for holding said container in engagement with said socket.

10. The system in accordance with claim 1 wherein said container is translucent.

11. The system in accordance with claim 1 further comprising electrical connectors coupled to said circuit to receive current from a power source and to provide said current to said heater.

* * * * *